(12) United States Patent
Gorochow et al.

(10) Patent No.: US 12,011,171 B2
(45) Date of Patent: Jun. 18, 2024

(54) SYSTEMS AND METHODS FOR INHIBITING PREMATURE EMBOLIC IMPLANT DEPLOYMENT

(71) Applicant: DePuy Synthes Products, Inc., Raynham, MA (US)

(72) Inventors: Lacey Gorochow, Miami, FL (US); Ruijiao Xu, Miami Lakes, FL (US); Daniel Solaun, Miami, FL (US); David Blumenstyk, Miami, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 33 days.

(21) Appl. No.: 17/569,632

(22) Filed: Jan. 6, 2022

(65) Prior Publication Data

US 2023/0210531 A1 Jul. 6, 2023

(51) Int. Cl.
*A61B 17/12* (2006.01)
*A61B 17/00* (2006.01)
*A61M 25/00* (2006.01)

(52) U.S. Cl.
CPC ............ *A61B 17/12022* (2013.01); *A61B 2017/00323* (2013.01); *A61B 2017/12054* (2013.01); *A61B 17/12113* (2013.01); *A61B 17/1214* (2013.01); *A61M 25/005* (2013.01)

(58) Field of Classification Search
CPC ...... A61B 2017/12054; A61B 17/1214; A61B 17/12113; A61B 17/12022; A61B 17/58; A61M 29/00
See application file for complete search history.

(56) References Cited

U.S. PATENT DOCUMENTS

| 2,220,203 A | 2/1939 | Branin |
| 3,429,408 A | 2/1969 | Maker et al. |
| 4,858,810 A | 8/1989 | Intlekofer et al. |

(Continued)

FOREIGN PATENT DOCUMENTS

| CN | 104203341 A | 12/2014 |
| CN | 106456422 A | 2/2017 |

(Continued)

OTHER PUBLICATIONS

Extended European Search Report issued in European Patent Application No. 23150409.3 dated Jun. 2, 2023.

*Primary Examiner* — Tuan V Nguyen
*Assistant Examiner* — Osama Nemer
(74) *Attorney, Agent, or Firm* — TROUTMAN PEPPER HAMILTON SANDERS LLP

(57) ABSTRACT

Disclosed herein are various exemplary systems, devices, and methods for inhibiting premature implant deployment. The delivery member can include a body including a lumen extending therethrough, the body including a compressed distal portion. The delivery member can include a pull wire extending through the lumen. The pull wire can include a pull wire portion that extends radially to abut a sidewall of the body to provide frictional resistance against the body. The pull wire can be positioned to secure the implantable medical device to the delivery member, and the pull wire portion can be effective to inhibit premature detachment of the implant by inhibiting proximal translation of the pull wire due to the frictional resistance provided by the pull wire portion against the body.

20 Claims, 7 Drawing Sheets

(56) References Cited

U.S. PATENT DOCUMENTS

| | | | |
|---|---|---|---|
| 5,108,407 A | 4/1992 | Geremia et al. | |
| 5,122,136 A | 6/1992 | Guglielmi et al. | |
| 5,234,437 A | 8/1993 | Sepetka | |
| 5,250,071 A | 10/1993 | Palermo | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,392,791 A * | 2/1995 | Nyman | A61N 1/056 |
| | | | 600/585 |
| 5,484,409 A | 1/1996 | Atkinson et al. | |
| 5,569,221 A | 10/1996 | Houser et al. | |
| 5,899,935 A | 5/1999 | Ding | |
| 5,925,059 A | 7/1999 | Palermo et al. | |
| 6,113,622 A | 9/2000 | Hieshima | |
| 6,203,547 B1 | 3/2001 | Nguyen et al. | |
| 6,391,037 B1 | 5/2002 | Greenhalgh | |
| 6,454,780 B1 | 9/2002 | Wallace | |
| 6,506,204 B2 | 1/2003 | Mazzocchi | |
| 6,561,988 B1 | 5/2003 | Turturro et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,384,407 B2 | 6/2008 | Rodriguez et al. | |
| 7,708,754 B2 | 5/2010 | Balgobin et al. | |
| 7,708,755 B2 | 5/2010 | Davis, III et al. | |
| 7,799,052 B2 | 9/2010 | Balgobin et al. | |
| 7,811,305 B2 | 10/2010 | Balgobin et al. | |
| 7,819,891 B2 | 10/2010 | Balgobin et al. | |
| 7,819,892 B2 | 10/2010 | Balgobin et al. | |
| 7,901,444 B2 | 3/2011 | Slazas | |
| 7,985,238 B2 | 7/2011 | Balgobin et al. | |
| 8,062,325 B2 | 11/2011 | Mitelberg et al. | |
| 8,333,796 B2 | 12/2012 | Tompkins et al. | |
| 8,926,650 B2 | 1/2015 | Que et al. | |
| 8,956,381 B2 | 2/2015 | Que et al. | |
| 9,155,540 B2 | 10/2015 | Lorenzo | |
| 9,232,992 B2 | 1/2016 | Heidner | |
| 9,314,326 B2 | 4/2016 | Wallace et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,120 B2 | 5/2017 | Lagodzki et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,918,718 B2 | 3/2018 | Lorenzo | |
| 10,149,676 B2 | 12/2018 | Mirigian et al. | |
| 10,285,710 B2 | 5/2019 | Lorenzo et al. | |
| 10,292,851 B2 | 5/2019 | Gorochow | |
| 10,420,563 B2 | 9/2019 | Hebert et al. | |
| 10,517,604 B2 | 12/2019 | Bowman et al. | |
| 10,668,258 B1 | 6/2020 | Calhoun et al. | |
| 10,806,402 B2 | 10/2020 | Cadieu et al. | |
| 10,806,461 B2 | 10/2020 | Lorenzo | |
| 2001/0049519 A1 | 12/2001 | Holman et al. | |
| 2002/0072705 A1 | 6/2002 | Vrba et al. | |
| 2002/0165569 A1 | 11/2002 | Ramzipoor et al. | |
| 2003/0009208 A1 | 1/2003 | Snyder et al. | |
| 2004/0034363 A1 | 2/2004 | Wilson et al. | |
| 2004/0059367 A1 | 3/2004 | Davis et al. | |
| 2004/0087964 A1 | 5/2004 | Diaz et al. | |
| 2006/0025801 A1 | 2/2006 | Lulo et al. | |
| 2006/0064151 A1 | 3/2006 | Guterman | |
| 2006/0100687 A1 | 5/2006 | Fahey et al. | |
| 2006/0116711 A1 | 6/2006 | Elliott et al. | |
| 2006/0116714 A1 | 6/2006 | Sepetka et al. | |
| 2006/0135986 A1 | 6/2006 | Wallace et al. | |
| 2006/0206139 A1 | 9/2006 | Tekulve | |
| 2006/0241685 A1 * | 10/2006 | Wilson | A61B 17/12113 |
| | | | 606/200 |
| 2006/0247677 A1 | 11/2006 | Cheng et al. | |
| 2006/0276824 A1 | 12/2006 | Mitelberg et al. | |
| 2006/0276825 A1 | 12/2006 | Mitelberg et al. | |
| 2006/0276826 A1 | 12/2006 | Mitelberg et al. | |
| 2006/0276827 A1 | 12/2006 | Mitelberg et al. | |
| 2006/0276830 A1 | 12/2006 | Balgobin et al. | |
| 2006/0276833 A1 | 12/2006 | Balgobin et al. | |
| 2007/0010850 A1 | 1/2007 | Balgobin et al. | |
| 2007/0055302 A1 | 3/2007 | Henry et al. | |
| 2007/0083132 A1 | 4/2007 | Sharrow | |
| 2007/0233168 A1 | 10/2007 | Davis et al. | |
| 2007/0270903 A1 | 11/2007 | Davis, III et al. | |
| 2008/0027561 A1 | 1/2008 | Mitelberg et al. | |
| 2008/0045997 A1 | 2/2008 | Balgobin et al. | |
| 2008/0082176 A1 * | 4/2008 | Slazas | A61B 17/12022 |
| | | | 623/23.72 |
| 2008/0097462 A1 | 4/2008 | Mitelberg et al. | |
| 2008/0119887 A1 | 5/2008 | Que et al. | |
| 2008/0269721 A1 * | 10/2008 | Balgobin | A61B 17/1214 |
| | | | 29/469 |
| 2008/0281350 A1 | 11/2008 | Sepetka | |
| 2008/0300616 A1 | 12/2008 | Que et al. | |
| 2008/0306503 A1 | 12/2008 | Que et al. | |
| 2009/0062726 A1 | 3/2009 | Ford et al. | |
| 2009/0099592 A1 | 4/2009 | Buiser et al. | |
| 2009/0312748 A1 | 12/2009 | Johnson et al. | |
| 2010/0094395 A1 | 4/2010 | Kellett | |
| 2010/0114017 A1 | 5/2010 | Lenker et al. | |
| 2010/0206453 A1 | 8/2010 | Leeflang et al. | |
| 2010/0324649 A1 | 12/2010 | Mattsson | |
| 2011/0092997 A1 | 4/2011 | Kang | |
| 2011/0118776 A1 | 5/2011 | Chen et al. | |
| 2011/0202085 A1 | 8/2011 | Loganathan et al. | |
| 2011/0295303 A1 | 12/2011 | Freudenthal | |
| 2012/0035707 A1 | 2/2012 | Mitelberg et al. | |

(56) References Cited

U.S. PATENT DOCUMENTS

| | | |
|---|---|---|
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1* | 7/2012 | Yamanaka ........ A61B 17/12145 606/200 |
| 2012/0179194 A1* | 7/2012 | Wilson ............ A61B 17/12154 606/200 |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0243883 A1 | 8/2014 | Tsukashima et al. |
| 2014/0277084 A1* | 9/2014 | Mirigian ............ A61B 17/0467 606/200 |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalcaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1* | 11/2016 | Hebert ............ A61B 17/12154 |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1* | 4/2017 | Dias ................ A61B 17/12113 |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1* | 10/2018 | Hebert .................. A61B 50/00 |
| 2018/0325706 A1 | 11/2018 | Hebert et al. |
| 2019/0142565 A1* | 5/2019 | Follmer .......... A61B 17/12113 606/200 |
| 2019/0159784 A1 | 5/2019 | Sananes et al. |
| 2019/0192162 A1 | 6/2019 | Lorenzo et al. |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2021/0001082 A1 | 1/2021 | Lorenzo et al. |
| 2021/0045759 A1* | 2/2021 | Merhi ............ A61B 17/00234 |
| 2021/0085498 A1 | 3/2021 | Nygaard et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0346002 A1 | 11/2021 | Lorenzo et al. |

(56) References Cited

U.S. PATENT DOCUMENTS

2021/0353299 A1    11/2021  Hamel et al.
2022/0087685 A1*    3/2022  Mayer .............. A61B 17/12113

FOREIGN PATENT DOCUMENTS

| | | | |
|---|---|---|---|
| CN | 112168263 A * | 1/2021 | ....... A61B 17/12022 |
| EP | 1985244 A2 | 10/2008 | |
| EP | 2498691 | 9/2012 | |
| EP | 3061412 A2 * | 8/2016 | ....... A61B 17/12113 |
| EP | 3092956 A1 | 11/2016 | |
| EP | 3501427 A1 | 6/2019 | |
| EP | 3799803 A1 | 4/2021 | |
| EP | 3854321 A1 | 7/2021 | |
| EP | 1188414 A1 | 3/2022 | |
| EP | 4119065 A1 | 1/2023 | |
| JP | 2006-334408 A | 12/2006 | |
| JP | 2012-523943 A | 10/2012 | |
| JP | 2013-78584 A | 5/2013 | |
| JP | 2014-399 A | 1/2014 | |
| WO | WO 2007/070793 A2 | 6/2007 | |
| WO | 2008064209 A1 | 5/2008 | |
| WO | WO 2009/132045 A2 | 10/2009 | |
| WO | WO 2012/158152 A1 | 11/2012 | |
| WO | WO 2016/014985 A1 | 1/2016 | |
| WO | WO 2017/066386 A1 | 4/2017 | |
| WO | WO 2018/022186 A1 | 2/2018 | |
| WO | WO 2020/148768 A1 | 7/2020 | |

* cited by examiner

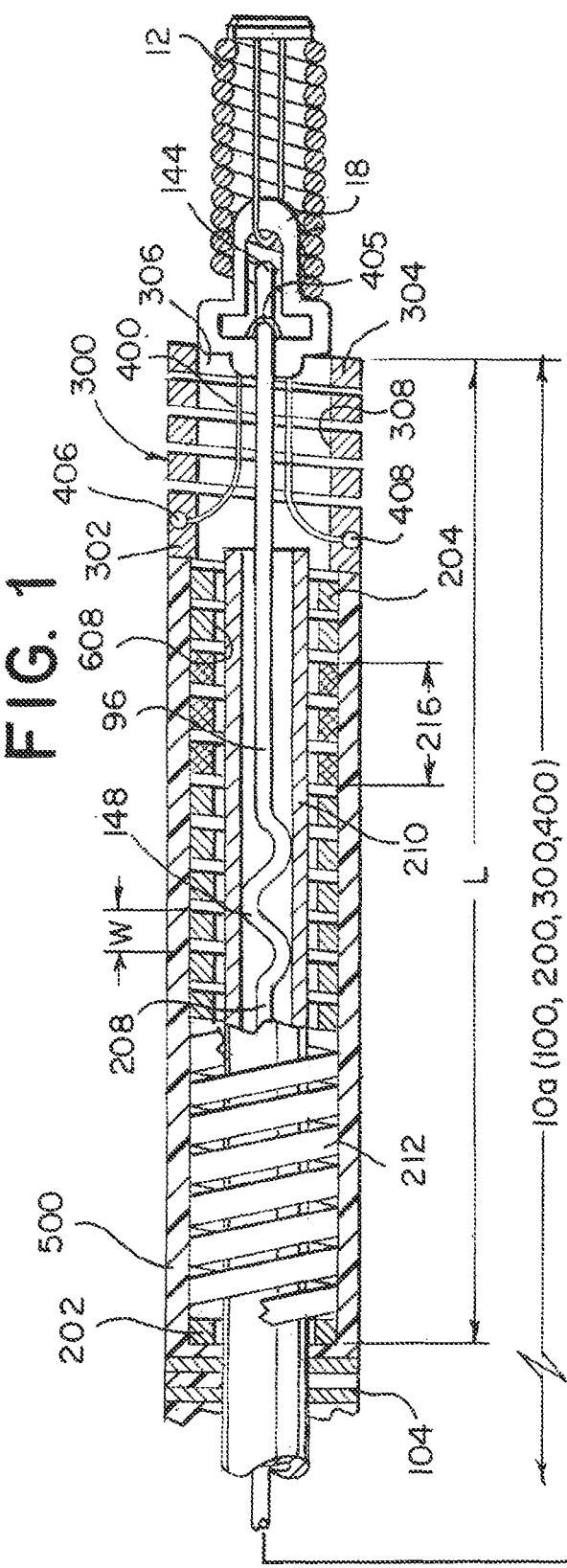
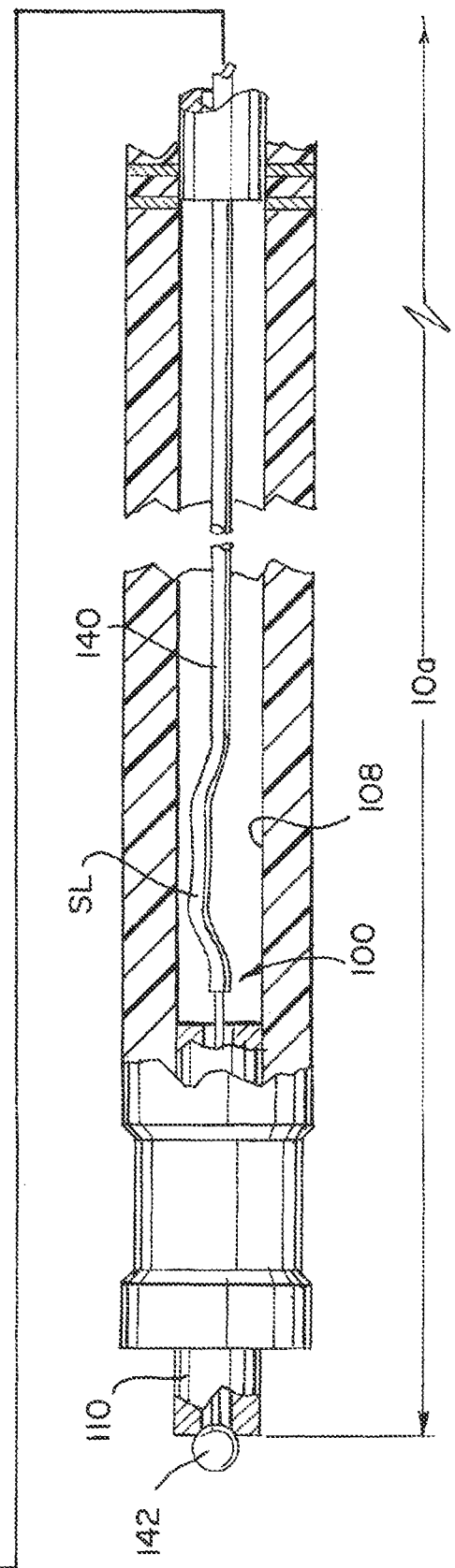
FIG. 1

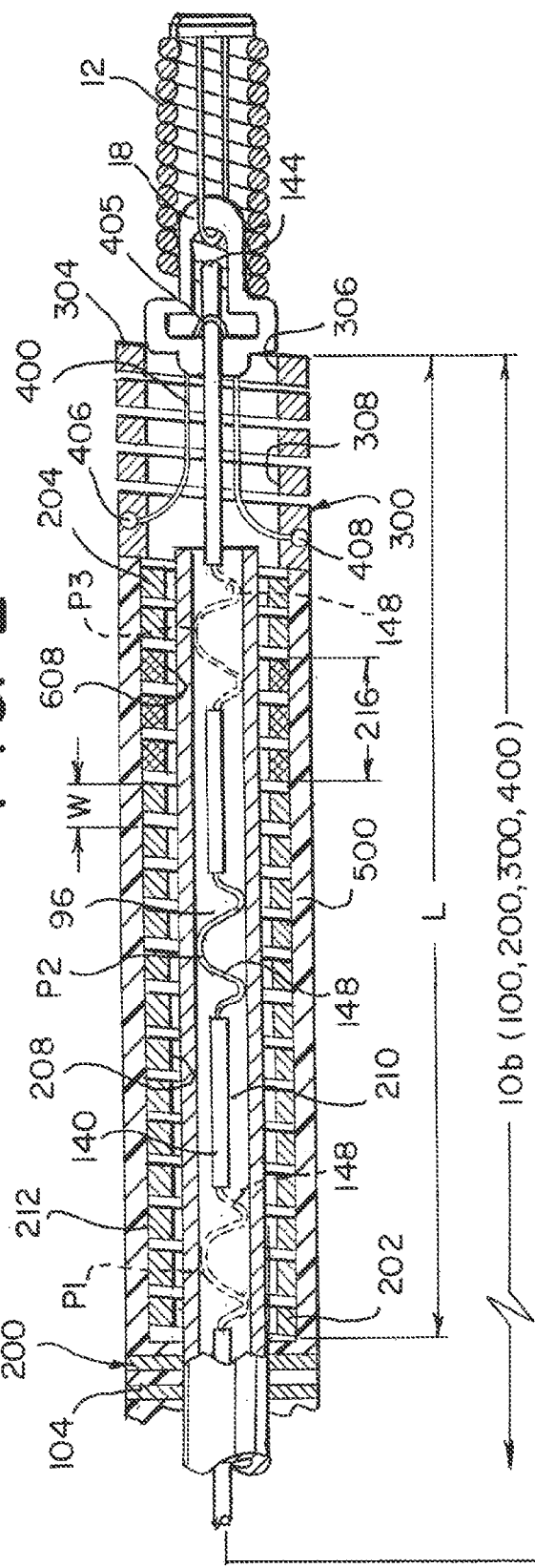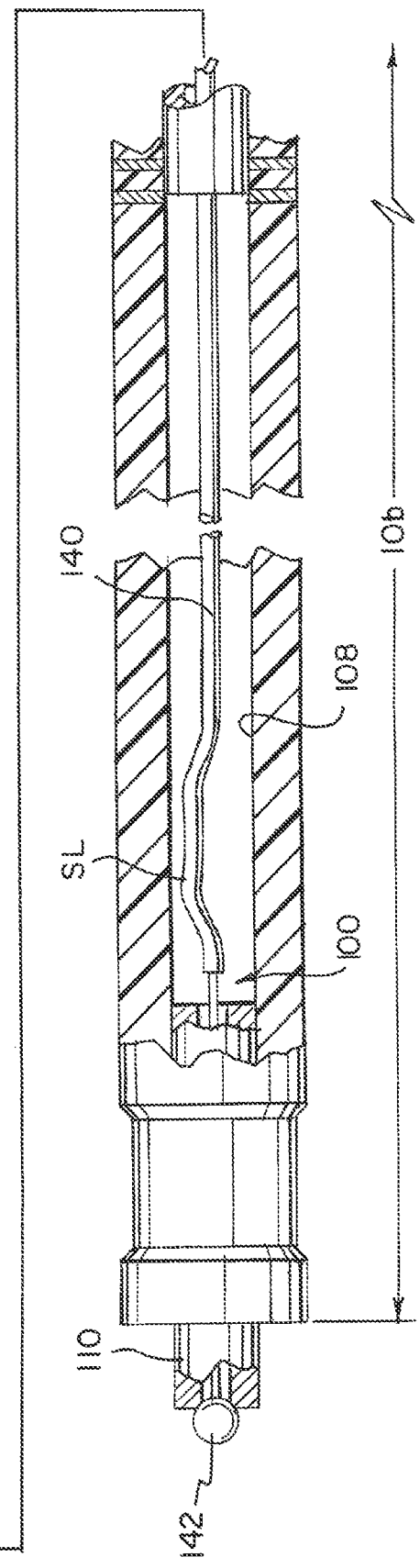
FIG. 2

FIG. 3A
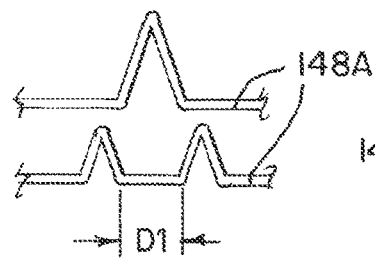
FIG. 3B
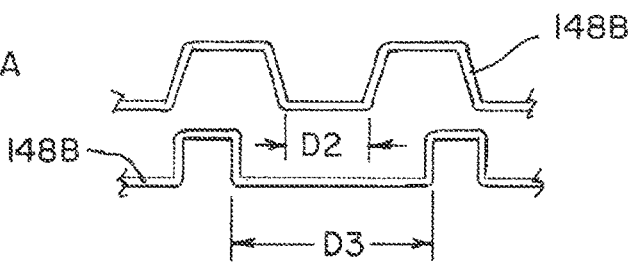
FIG. 3C
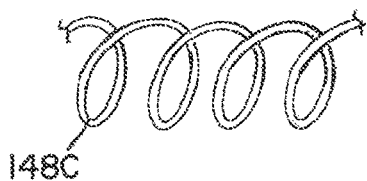
FIG. 3D
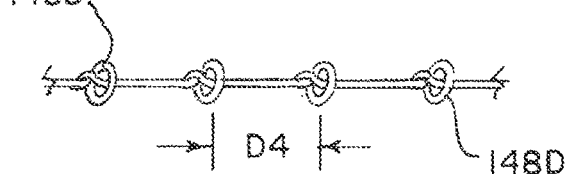
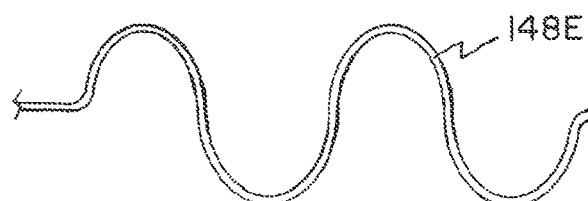
FIG. 3E
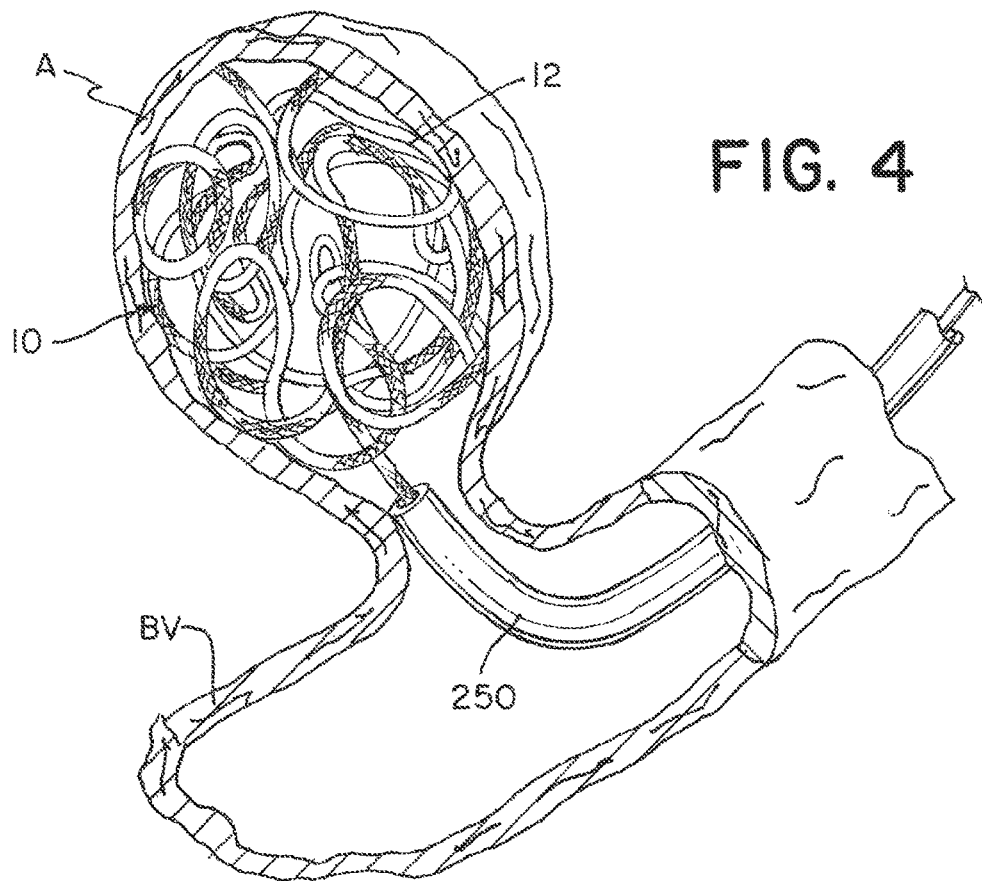
FIG. 4

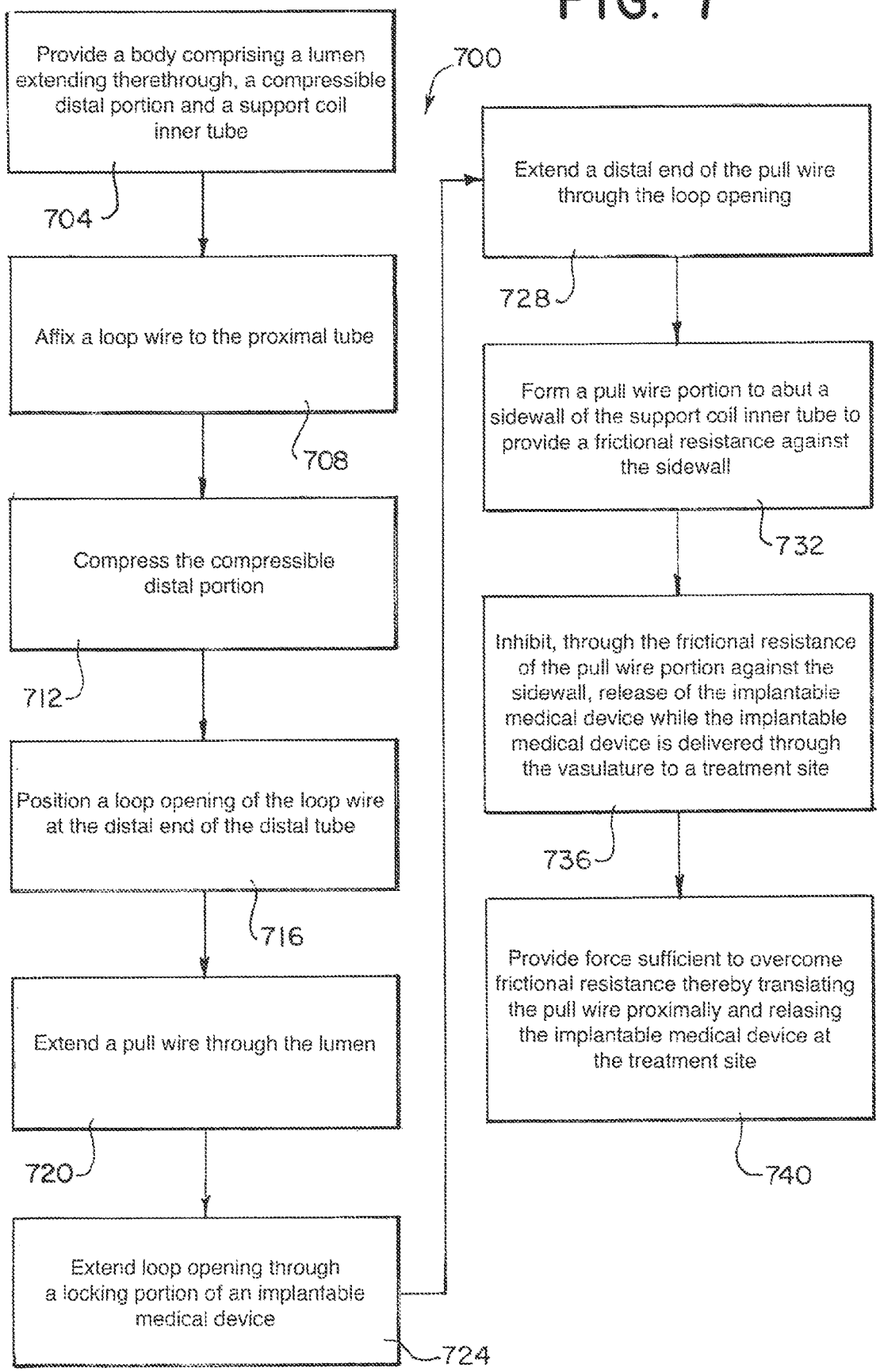

SYSTEMS AND METHODS FOR INHIBITING PREMATURE EMBOLIC IMPLANT DEPLOYMENT

FIELD OF INVENTION

The present invention relate to aneurysm treatment devices and more particularly, to improved delivery systems for embolic implants that prevent premature implant deployment.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

One issue with current catheter-based delivery systems is premature detachment of the implantable device. Premature detachment occurs when the implant is detached from the delivery system before reaching the treatment site. This may occur due to the tortuosity experienced by the delivery system as it passes through the vasculature of the patient, which can cause an increase in friction between the "pull wire" and the delivery system causing the pull wire to move proximally while the delivery system is moving distally.

Accordingly, there is a need for an improved implant delivery system that prevents premature detachment of the implant as it is delivered through tortuous vasculature. This disclosure is directed to this and other considerations.

SUMMARY

Disclosed herein are various exemplary systems, devices, and methods for inhibiting premature implant deployment. The delivery member can include a body including a lumen extending therethrough, the body including a compressed distal portion. The delivery member can include a pull wire extending through the lumen. The pull wire can include a pull wire portion that extends radially to abut a sidewall of the body to provide frictional resistance against the body. The pull wire can be positioned to secure the implantable medical device to the delivery member, and the pull wire portion can be effective to inhibit premature detachment of the implant by inhibiting proximal translation of the pull wire due to the frictional resistance provided by the pull wire portion against the body.

In one aspect, a delivery member for delivering an implantable medical device to a target location of a body vessel is disclosed. The delivery member can include a body that includes a lumen extending therethrough and a compressed distal portion. The delivery member can include a pull wire that extends through the lumen. The pull wire can include a pull wire portion that extends radially to abut a sidewall of a support coil inner tube to provide frictional resistance. The pull wire can be positioned to secure the implantable medical device to the delivery member. The pull wire portion can be effective to inhibit premature detachment of the implantable medical device by inhibiting proximal translation of the pull wire due to the frictional resistance provided by the pull wire portion against the sidewall.

In some embodiments, the pull wire is movable to release the implantable medical device from the delivery member. In some embodiments, the pull wire portion includes a shaped feature selected from a trapezoidal-shaped feature, a triangular-shaped feature, a corkscrew-shaped feature, a knot-shaped feature, or a wave-shaped feature.

In some embodiments, the pull wire is made of stainless steel. In some embodiments, the pull wire is made of a memory shape alloy. In some embodiments, the pull wire is coated with a polytetrafluoroethylene (PTFE) coating. In some embodiments, the PTFE coating is selectively removed from the pull wire portion.

In some embodiments, the pull wire portion remains in contact with the sidewall of the body as the implantable medical device is delivered to the target location of the body vessel.

In some embodiments, the delivery member can include a loop wire that includes a first end that is affixed to the body and a loop opening that is positioned approximate a distal end of the compressed distal portion.

In some embodiments, the loop wire is stretch resistant, and the loop wire is under tension when the implantable medical device is secured to the delivery member. In some embodiments, the body further includes a flexible coil that is disposed in a proximal direction from the distal portion. The loop wire can inhibit elongation of the compressed distal portion.

In some embodiments, the delivery member can include a sleeve that extends along a majority of the flexible coil.

In another aspect, a method is disclosed. The method can include providing a body that includes a lumen extending therethrough and a compressible distal portion. The method can include compressing the compressible distal portion. The method can include extending a pull wire through the lumen. The method can include securing a distal end of the pull wire to an implantable medical device. The method can include forming a pull wire portion of the pull wire to abut a sidewall of a support coil inner tube to provide a frictional resistance against the sidewall.

In some embodiments, the method can include inhibiting, through the frictional resistance of the pull wire portion against the sidewall, release of the implantable medical device while the implantable medical device is delivered through the vasculature to a treatment site and providing a force sufficient to overcome the frictional resistance of the pull wire portion against the sidewall, thereby translating the pull wire proximally and releasing the implantable medical device at the treatment site.

In some embodiments, the method can include affixing a loop wire to the body, positioning a loop opening in the loop wire approximate a distal end of the compressible distal portion while the loop wire is affixed to the body such that the loop wire is extended through the lumen, and extending the loop opening through a locking portion of an implantable medical device.

In some embodiments, the pull wire portion can include a shaped feature selected from a trapezoidal-shaped feature, a triangular-shaped feature, a corkscrew-shaped feature, a knot-shaped feature, or a wave-shaped feature.

In some embodiments, the pull wire can include a memory shape alloy.

In some embodiments, inhibiting release of the implantable medical device can include the pull wire portion remaining in contact with the sidewall as the implantable medical device is delivered to the target location of the body vessel.

In some embodiments, the method can include coating the pull wire with a polytetrafluoroethylene (PTFE) coating and selectively removing the PTFE coating from the pull wire portion.

In some embodiments, the method can include connecting a distal end of a proximal hypotube to a flexible coil, connecting a distal end of the flexible coil to a proximal end of the compressible distal portion of the body, connecting the proximal tube, flexible coil, and compressible distal hypotube to provide the body which includes a lumen extending through the proximal tube, flexible coil, and the compressed distal portion, and positioning a sleeve to extend along a majority of the flexible coil, thereby inhibiting radial expansion of the flexible coil.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 an illustration of a delivery member and implant, according to aspects of the present invention.

FIG. 2 is an illustration of another delivery member and implant, according to aspects of the present invention.

FIGS. 3A-3E are illustrations of exemplary pull wire portions, according to aspects of the present invention.

FIG. 4 is an illustration of embolic coils being positioned within an aneurysm according to aspects of the present invention.

FIG. 7 is a flowchart of an example method of using the delivery member, according to aspects of the present invention.

DETAILED DESCRIPTION

Figure 5:
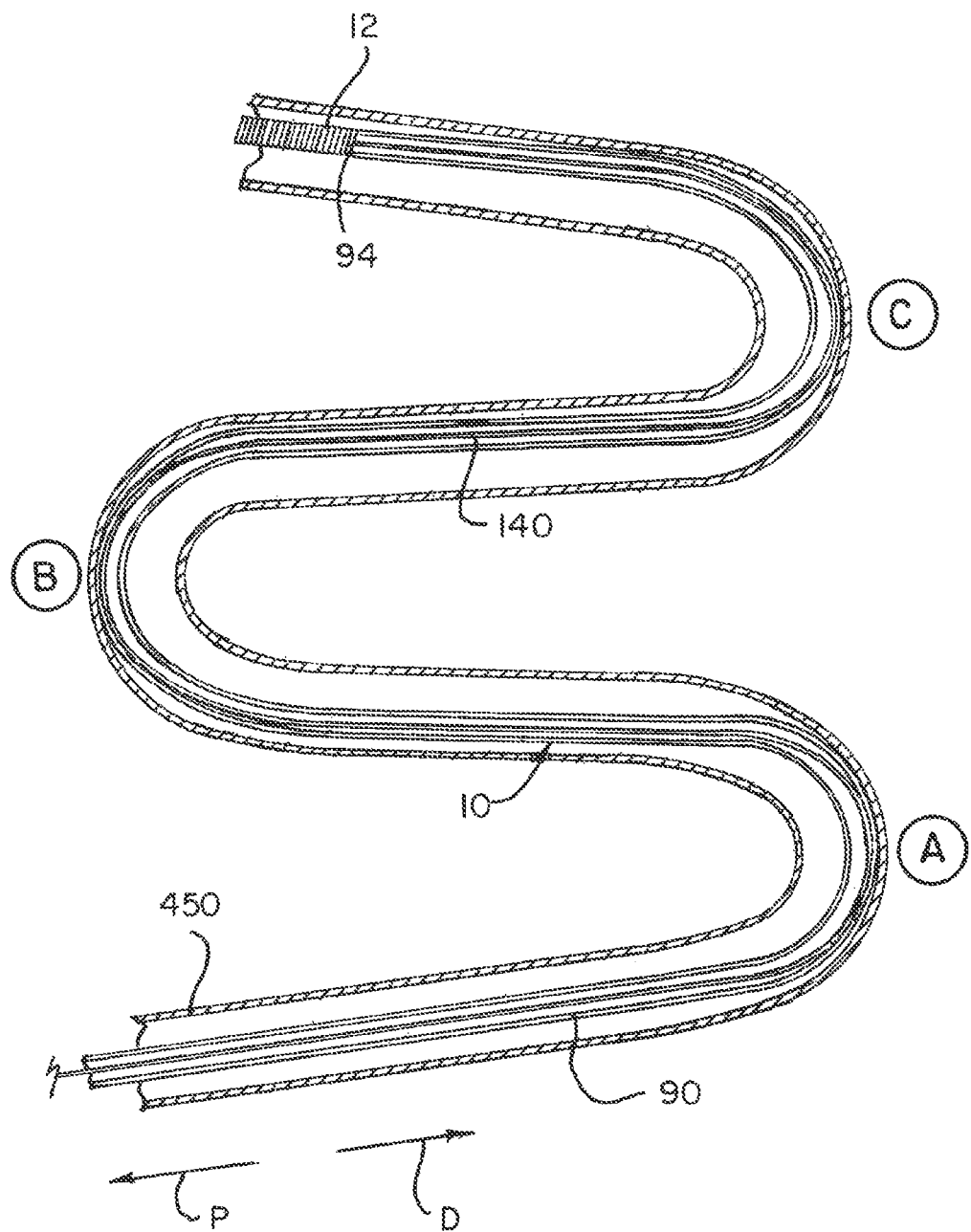
FIG. 5 is an illustration of a delivery member navigating a body lumen according to aspects of the present invention.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Turning to the figures, as illustrated in FIGS. 1 and 2 an example delivery member 10a, 10b, can include a proximal tube 100, a coiled section 200, a compressible distal portion 300, a sleeve 500 surrounding the coiled section, and a loop wire 400 extending through the compressed distal portion 300. The delivery member 10a, 10b can have a lumen 608 therethrough extending through the proximal tube 100, coiled section 200, and compressible distal portion 300. That is, the proximal tube 100 can have a lumen 108 therethrough, the coiled section 200 can have a lumen 208 therethrough, the compressible distal portion 300 can have a lumen 308 therethrough, and the lumens 108, 208, 308 can be contiguous to form the lumen 608 through the delivery member 10a, 10b. The proximal tube 100 can have a distal end 104 connected to a proximal end 202 of the coiled section 200 and a distal end 204 of the coiled section 200 can be connected to a proximal end 302 of the compressible distal portion 300. Proximal tube 100, coiled section 200, and compressed distal portion 300 can be collectively referred to as body 90.

The compressible distal portion 300 can be formed from a spiral cuts 306 made within the compressible distal portion 300. The compressible portion 300 can be axially adjustable between an elongated condition and a compressed condition. The compressible portion 300 can be formed from a spiral-cut portion of the tube 300, formed by a laser cutting operation. Additionally, or alternatively, the compressible portion can be formed of a wound wire, spiral ribbon, or other arrangement allowing axial adjustment according to the present invention. Preferably, compressible portion 300 is in the elongated condition at rest and automatically or resiliently returns to the elongated condition from a compressed condition, unless otherwise constrained.

When the delivery member 10a, 10b, is assembled, the coiled section 200 and sleeve 500 can be more flexible than the compressed distal portion 300 and the proximal tube 100. One way to measure flexibility is to perform a three-point bend test wherein a portion of the delivery member 10a, 10b is held fixed at two end points, a force is applied perpendicularly to the member 10a, 10b centrally between the points, and flexibility is quantified by the length of deflection of the delivery member 10a, 10b caused by the force. When measured in this way, in some examples, the coiled section 200 and sleeve can be about 1.5 times more flexible than the compressed distal portion 300 and about 20 times more flexible than the proximal tube 100. That is, when the three-point test is performed identically on the three sections 100, 200, and 300, the coiled section deflect over a length that is about 1.5 times the deflection of the distal hypotube and about 20 times the length of deflection of the proximal hypotube. Flexibility can be measured in other ways as would be appreciated and understood by a person having pertinent skill in the requisite art. When the delivery member 10a, 10b is assembled, the coiled section 200 and sleeve 500 can be more flexible than the distal hypotube and the proximal hypotube as flexibility is determined by other means as would be known to a person having pertinent skill in the relevant art.

The coiled section can be formed primarily of a non-radiopaque material such as steel and can include a radiopaque section 216 made of a radiopaque material such as platinum and/or tungsten. The radiopaque section 216 can be positioned a predetermined distance from a distal end 304 of the delivery member 10a, 10b so that a physician can readily visualize the placement of the distal portion of the delivery member during a treatment procedure. The proximal section 212, radiopaque section 216 can be concentrically welded.

Proximal tube 100 can extend a majority of the length of the delivery member 10a, 10b with the coiled section 200 and the compressible distal portion 300 forming a length L that is sufficient to absorb a majority of push-back that can occur during placement of an implant at a treatment site. In some example the length L can measure between about 30 cm and about 50 cm, or more specifically, about 40 cm. According to some embodiments, the wire of coil 200 can have a width W measuring within a range including about 0.8 mils and 5 mils (about 20 nm to about 130 nm).

Delivery members 10a, 10b manufactured according to the illustrations in FIG. 1 and FIG. 2 are demonstrated to have a flexibility of about 25% to about 40% greater than competing delivery systems.

Within the proximal tube 100 of delivery members 10a, 10b can be disposed a proximal inner tube 110. Proximal inner tube 110 can provide structural rigidity to the proximal tube 100. Both delivery members 10a, 10b can include a pull wire 140 extending through lumen 608. A proximal end of the pull wire 140 can include a pull wire bead 142 which can be sized to interface with proximal inner tube 110 such that pull wire bead 142 is retained on a proximal end of proximal tube 100. A distal end 144 of the pull wire 140 can be configured to secure an implantable medical device 12 to the delivery member 10a, 10b. For example, the loop wire 400 can include a loop wire opening 405 that is positioned through a locking portion 18 of the implantable medical device 12. The distal end 144 of the pull wire 104 can then be positioned through the loop opening 405 to thereby secure the implantable medical device 12 to the delivery member 10a, 10b. Proximal ends 406, 408 of loop wire 400 can be attached to a proximal end 302 of the compressible distal portion 300. Disposed within support coil lumen 208 can be a support coil inner tube 210. Support coil inner tube 210 can provide structural rigidity to the support coil 200. Additionally, support coin inner tube 210 can include a sidewall 96.

With respect to FIGS. 1 and 2, delivery member 10a, 10b can include a pull wire portion 148 that is configured to abut a sidewall 96 of support coil inner tube 210. Pull wire portion 148 can be of any convenient shape/configuration, with exemplary configurations being discussed in more detail with respect to FIGS. 3A-3E and FIG. 8. As delivery member 10a, 10b is delivered through the vasculature of a patient to a target location of a body vessel, the pull wire 140 can experience a force that can cause the pull wire 140 to drift proximally with respect to the body 90 of the delivery member 10a, 10b. To aid in the prevention of premature detachment of the implantable medical device 12 from the detachment member 10a, 10b, a slack length SL of pull wire 140 can be included and disposed within proximal tube lumen 108. Accordingly, some proximal drift of pull wire 140 can merely remove some or all of slack length SL from the pull wire 140. Additionally, pull wire portion 148 can provide a frictional resistance between the pull wire 140 and the sidewall 96 of the support coil inner tube 210. As shown in FIGS. 1-2, pull wire portion 148 can include a portion of pull wire 140 that extends radially to abut the sidewall 96, and a portion that extends parallel to sidewall 96 and is in frictional contact with sidewall 96. The shape and configuration of pull wire portion 148 can be varied as would be understood by a person having skill in the pertinent art. Pull wire 140 can be constructed out of any suitable material, for example, pull wire 140 can be constructed of stainless steel or memory shape material, such as nitinol. According to some embodiments, pull wire 140 can additionally be coated with polytetrafluoroethylene (PTFE). In some embodiments, once pull wire 140 is coated with PTFE, the pull wire portion 148 can have the PTFE coating selectively removed in order to increase the frictional resistance provided by the pull wire portion 148 against sidewall 96. The pull wire portion 148 can be configured to remain in contact with the sidewall 96 of the body 90 while the implantable medical device 12 is delivered to the target implant location. Accordingly, the frictional resistance between pull wire portion 148 and sidewall 96 of the support coil inner tube 210 can be effective to prevent premature detachment of the implantable medical device from the delivery member 10a, 10b.

With respect to FIG. 1, the pull wire portion 148 is shown having the same thickness or diameter as the remainder of pull wire 140. However, according to some embodiments, pull wire portion 148 can have a coating selectively removed, which means that pull wire portion 148 can have a diameter or thickness smaller than the remainder of pull wire 140 according to some embodiments. According to some embodiments, the coating can be a polytetrafluoroethylene coating that is selectively removed from pull wire portion 148.

With respect to FIG. 2, a delivery member 10b is shown. The delivery member 10b can be similar to the delivery member 10a as shown in FIG. 1, except delivery member 10b can include a plurality of pull wire portions 148 instead of a single pull wire portion 148 as shown in FIG. 1. As shown in FIG. 2, pull wire portion 148 can be positioned anywhere between the dashed lines (e.g., within the support coil lumen 208) and can be placed in exemplary positions P1, P2, P3. In a preferred embodiment, delivery member 10a can include a single pull wire portion 148 that can be placed at position P3 to effectively prevent premature detachment of the implantable medical device 12 from the delivery member 10a. For delivery member 10b, pull wire portion 148 can be positioned anywhere within the dashed lines. In a preferred embodiment, delivery member 10b can include at least two pull wire portions 148 positioned anywhere between positions P1 and P3. As would be understood by a person having skill in the pertinent art, the positioning and number of pull wire portions 148 can be varied. Pull wire portion 148 as shown in FIG. 2 is shown with a coating selectively removed from the pull wire portion 148. The coating can be polytetrafluoroethylene (PTFE). However, in some embodiments the delivery system 10b can include pull wire portion(s) 148 that do not have a coating selectively removed from the pull wire portion(s) 148. In some embodiments, one or more pull wire portion(s) 148 of delivery system 10b can have a coating selectively removed while the remainder of pull wire portion(s) 148 do not have the coating selectively removed. In other words, any one of pull wire portions 148 can be coated or uncoated (e.g., at positions P1, P2, P3, and/or anywhere in between positions P1 and P3 of delivery system 10b).

FIGS. 3A-3E are illustrations of exemplary pull wire portions, according to aspects of the present invention. FIG. 3A shows a triangle shape of pull wire portion 148A. As shown in FIG. 3A, triangle shape pull wire portion 148A can be implemented as a single pre-formed shape, or pull wire portion 148A can include multiple repeats of the pre-formed shape. It is also understood that a person having pertinent skill in the art could vary a gap distance D1 between repeat sections of the pull wire portion 148A.

FIG. 3B shows a trapezoidal shape of pull wire portion 148B. As seen in FIG. 3B, gap distance can be varied between repeat trapezoids of the pull wire portion 148B. FIG. 3B shows the gap distance D2 in a first example and a gap distance D3 in a second example. FIG. 3C shows a pull wire portion 148C in the shape of a corkscrew. As shown in FIG. 3C, the corkscrew shape of pull wire portion 148C can have any number of rotations. In a preferable embodiment, the pull wire portion 148C may include between approximately 1 coil and 10 coils. FIG. 3D shows a pull wire portion 148D that is in a knot configuration. The knot of pull wire portion 148D can be varied in size as would be understood by a person having skill in the pertinent art. It is also understood that knot of pull wire portion 148D can be repeated with an appropriate gap distance D4 between each knot. According to some embodiments, the gap distance D1, D2, D3, D4 can be between approximately 0.001 inches and approximately 0.1 inches. According to some embodiments, the gap distance D1, D2, D3, D4, can be such that the pull wire portions 148 fit between the dashed lines of FIG. 2 (e.g., anywhere between position P1 and position P3).

FIG. 3E shows a pull wire portion 148E having a sine wave pattern. Similarly to the corkscrew of pull wire portion 148C, the pull wire portion 148E can be repeated between approximately 1 and approximately 10 repetitions. In any case, pull wire portion 148 can be sized and shaped to provide an appropriate frictional resistance between pull wire 140 and body 90 to prevent premature detachment of implant 12 from detachment member 10a, 10b.

FIG. 4 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

FIG. 5 illustrates positioning of an implant 12 such as an embolic coil suitable for aneurysm treatment, a guide catheter 450, and a delivery system 10 including a body 90, distal end 94, and a pull wire 140 within tortuous vasculature (vasculature not illustrated). At bends A, B, and C, the body 90 can extend to a sidewall of the guide catheter 450 on each outer curve of each bend, and likewise, the pull wire 140 can extend to a sidewall of the body 90 on each outer curve of each bend. During a procedure, the body 90 and pull wire 140 can be fed into the guide catheter 450 in the distal direction D, first passing through bend A, then bend B, and then bend C. As the body 90 and pull wire 140 navigate the bends, the pull wire portion 148 can provide frictional resistance between the pull wire 140 and the body 90 of delivery member 10a, 10b. This frictional resistance can prevent the proximal translation in a proximal direction P of pull wire 140 with respect to the body 90 of the delivery member 10a, 10b, which prevents the premature detachment of implant 12 from the delivery member 10a, 10b.

Figure 6A:
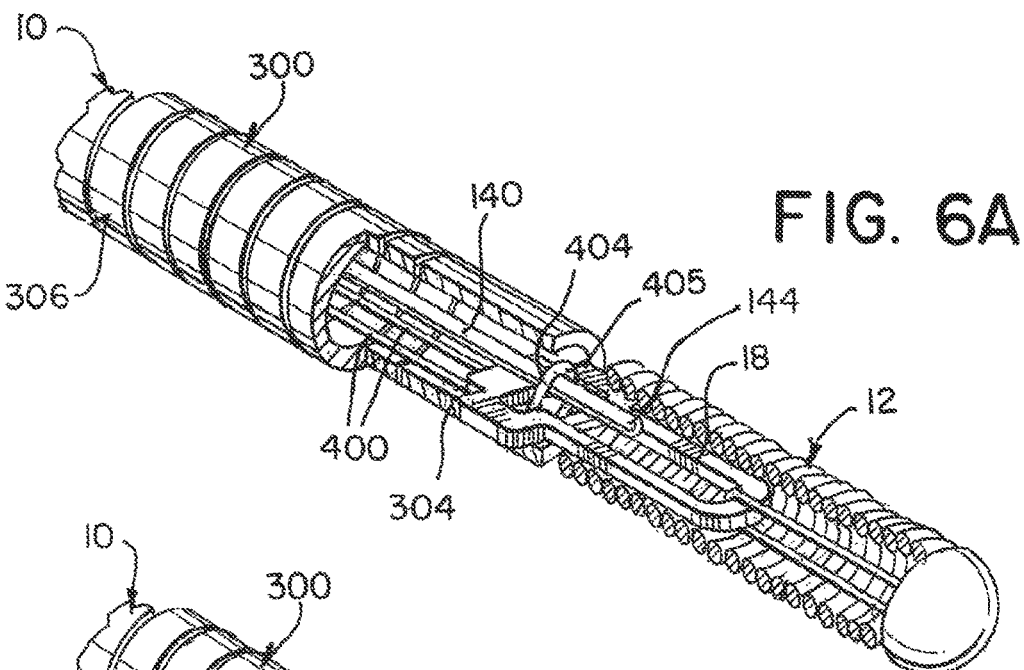
FIGS. 6A-6D illustrate a sequence of steps for releasing an embolic implant from the delivery member, according to aspects of the present invention.
Figure 6B:
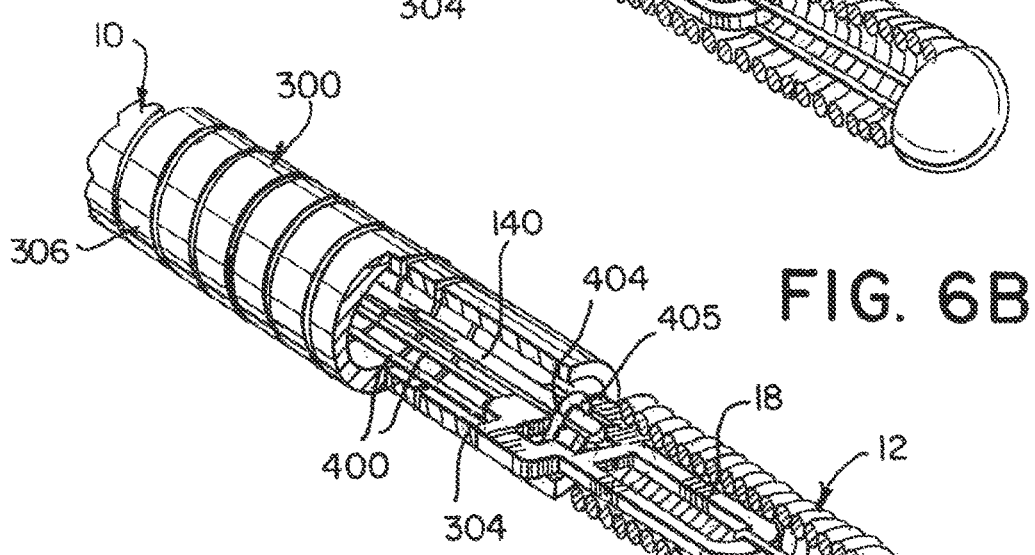
Figure 6C:
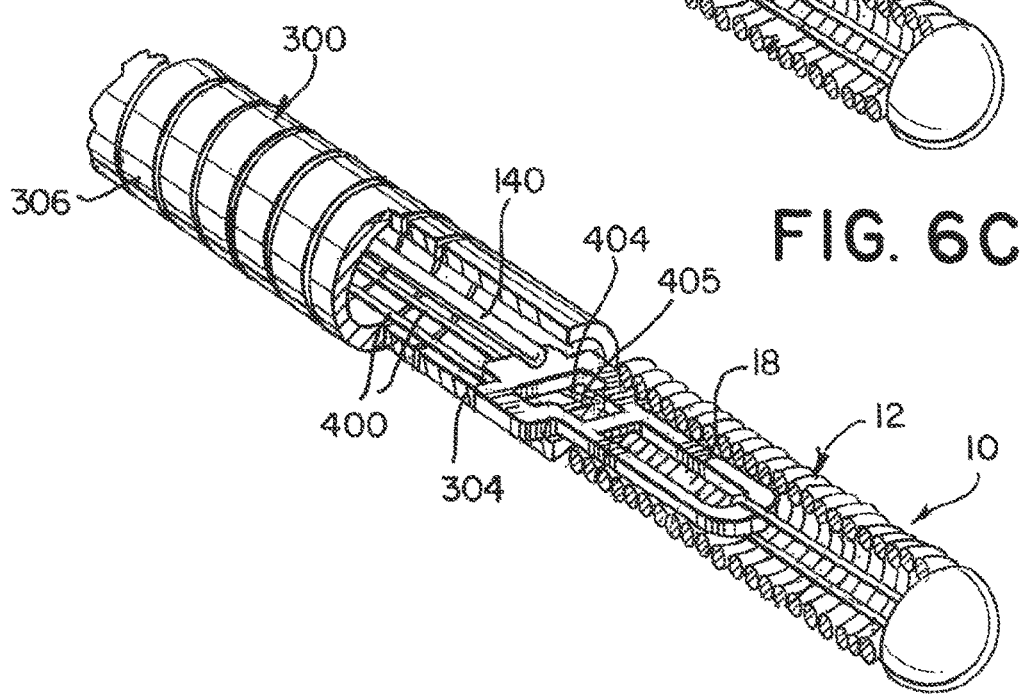
Figure 6D:
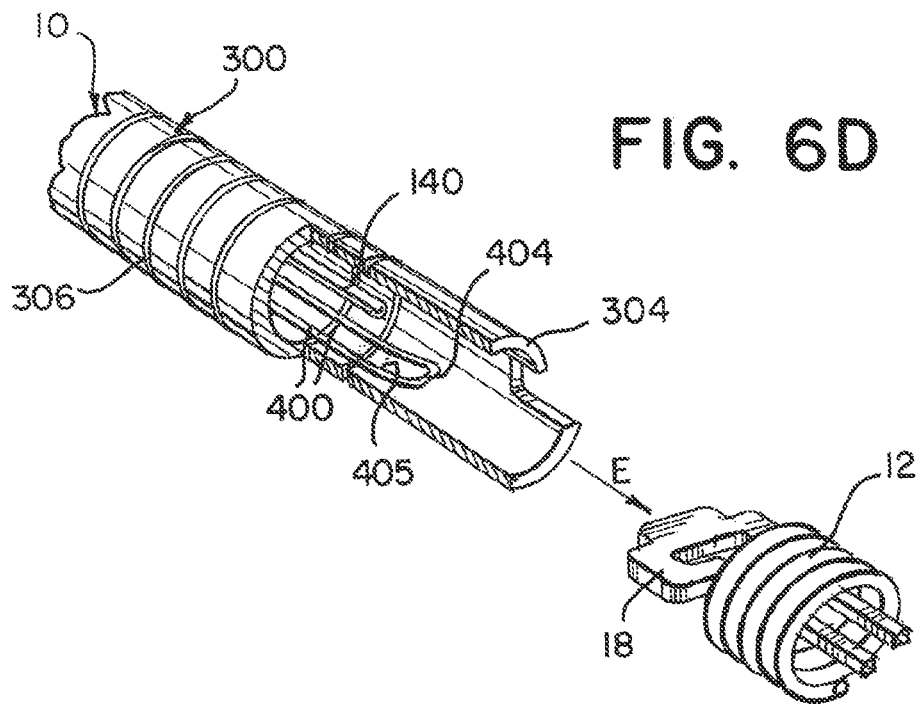

FIGS. 6A-6D illustrate a time sequence of steps for releasing an embolic implant 12 from a delivery member 10. The delivery member 10 can be configured such as illustrated in the previous figures and as otherwise described herein. FIG. 6A illustrates an engagement system including the loop wire 400 and pull wire 140 locked into a locking portion 18 of the medical device 12. The compressible portion 306 of the compressible distal portion 300 can be compressed and the loop wire 400 opening 405 at a distal end 404 of the loop wire 400 can be placed through the locking portion 18. When the pull wire 140 is put through the opening 405 the medical device 12 is now secure. FIG. 6B illustrates the pull wire 140 being drawn proximally to begin the release sequence for the medical device 12. FIG. 6C illustrates the instant the distal end 144 of the pull wire exits the opening 405 and the pull wire 140 is pulled free of the loop wire 400. The distal end 404 of the loop wire 400 falls away and exits the locking portion 18. As can be seen, there is now nothing holding the medical device 12 to the detachment system 10. FIG. 6D illustrates the end of the release sequence. Here, the compressible portion 306 has extended/returned to its original shape and "sprung" forward. An elastic force E is imparted by the distal end 305 of the compressible distal portion 300 to the medical device 12 to "push" it away to ensure a clean separation and delivery of the medical device 12.

The compressible portion 306 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the compressible distal portion 300.

FIG. 7 is a flowchart 700 of an example method of using the delivery system, according to aspects of the present invention. In block 704, the method includes providing a body that includes a lumen extending therethrough and a compressible distal portion 300. In block 708, the method can include affixing a loop wire 400 to the proximal tube 100. In block 712, the method can include compressing the compressible distal portion 300. In block 716, the loop opening 405 of the loop wire 400 can be positioned at the distal end 304 of the compressible distal portion 300 while the loop wire 400 is affixed to the body 90 such that the loop wire 400 is extended through lumen 608. In block 720, the pull wire 140 can be extended through the lumen 608. In block 724, the loop opening 405 can be extended through a locking portion 18 of an implantable medical device 12. In block 728, the distal end 144 of the pull wire 140 can be extended through the loop opening 405, which can effectively secure the implantable medical device 12 to the delivery member 10a, 10b. In block 732, the method can include forming a pull wire portion 148 to abut the sidewall 96 of support coil inner tube 210 to provide a frictional resistance against the sidewall 96. In block 736, the method includes inhibiting, through the frictional resistance of the pull wire portion 148 against the sidewall 96, release of the implantable medical device 12 while the implantable medical device 12 is delivered through the vasculature to a treatment site. In block 740, a force sufficient to overcome the frictional resistance of the pull wire portion 148 of against the sidewall 96 can be provided, which can cause the proximal translation of the pull wire 140 and release of the implantable medical device 12 at the treatment site.

According to some embodiments, inhibiting release of the implantable medical device 12 can include the pull wire portion 148 remaining in contact with the sidewall 96 as the implantable medical device 12 is delivered to the target location. In some embodiments, the method can include coating the pull wire 140 with a PTFE coating and selectively removing the PTFE coating from the pull wire portion 148.

In some embodiments, providing the body 90 can further include connecting a distal end 104 of a proximal hypotube 100 to a flexible coil 200, connecting a distal end 204 of the flexible coil 200 to a proximal end 302 of the compressible distal portion 300 of the body 90, connecting the proximal tube 100, flexible coil 200, and compressible distal portion 300 to provide the body, with the body including a lumen 608 that extends through the proximal tube 100, flexible coil 200, and the compressible distal portion 300. Finally, the method can include positioning a sleeve 500 to extend along a majority of the flexible coil 200 to inhibit radial expansion of the flexible coil.

Figure 8:
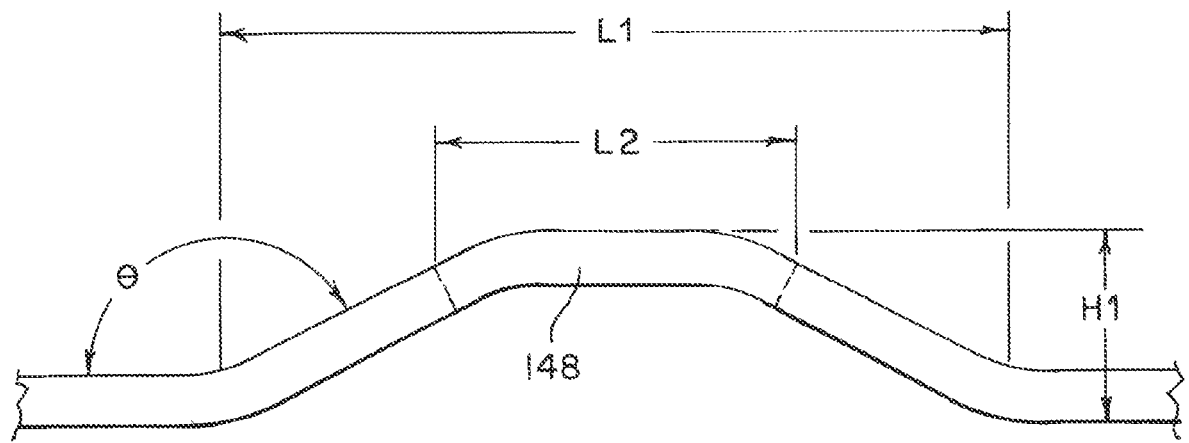
FIG. 8 is an illustration of an exemplary pull wire portion, according to aspects of the present invention.

FIG. 8 is an illustration of an exemplary pull wire portion, according to aspects of the present invention. According to some embodiments, the pull wire feature 148 can be "U" shaped, with a length L2 of the pull wire portion 148 abutting the sidewall 96 of the body 90 (e.g., the interference section of the pull wire portion 148), a length L1 of the pull wire portion 148 that corresponds to the length of the feature, and a distance H1 that shows the radial displacement of the pull wire portion 148 with respect to a remainder of the pull wire 140. In addition, the pull wire portion 148 may be offset from a remainder of the pull wire 140 by an angle θ.

According to some embodiments, the pull wire portion 148 can provide a frictional resistance between the pull wire 140 and the sidewall 96 of body 90 between approximately 7.8 gram-force to approximately 22 gram-force, and in a preferred embodiment, between approximately 9 gram-force to approximately 14 gram-force. In some embodiments, the angle θ can be between approximately 140 degrees to approximately 154 degrees. In some embodiments, the radial offset H1 of the pull wire portion 148 can be a distance selected from approximately 0.0065 inches to approximately 0.0079 inches. In some embodiments, the contact surface L2 of pull wire portion 148 can be a length between approximately 0.01 inches to approximately 0.0121 inches. In some embodiments, a total length L1 of the pull wire portion 148 can be a length between approximately 0.03 inches to approximately 0.36 inches.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A delivery member for delivering an implantable medical device to a target location of a body vessel, the delivery member comprising:
a body comprising a lumen extending therethrough, a compressed distal portion, and a support coil inner tube;
a pull wire extending through the lumen, the pull wire comprising a pull wire portion that extends radially to abut a sidewall of the support coil inner tube thereby providing frictional resistance against the support coil inner tube;
wherein the pull wire is positioned to secure the implantable medical device to the delivery member,
wherein the pull wire portion is effective to inhibit premature detachment of the implantable medical device by inhibiting proximal translation of the pull wire due to the frictional resistance provided by the pull wire portion against the support coil inner tube;
wherein the pull wire comprises a slack length at a proximal end of the pull wire and a straight portion distal of and approximate the slack length,
wherein a distal end of the pull wire comprises a straight portion, and
wherein the pull wire portion is proximal of and approximate the straight portion of the distal end of the pull wire.

2. The delivery member of claim 1, wherein the pull wire is proximally movable to release the implantable medical device from the delivery member.

3. The delivery member of claim 1, wherein the pull wire portion comprises a shaped feature selected from a trapezoidal-shaped feature, a triangular-shaped feature, a corkscrew-shaped feature, a knot-shaped feature, or a wave-shaped feature.

4. The delivery member of claim 1, wherein the pull wire comprises stainless steel.

5. The delivery member of claim 1, wherein the pull wire comprises a memory shape alloy.

6. The delivery member of claim 1, wherein the pull wire is coated with a polytetrafluoroethylene coating.

7. The delivery member of claim 6, wherein the polytetrafluoroethylene coating is selectively removed from the pull wire portion.

8. The delivery member of claim 1, wherein the pull wire portion remains in contact with the sidewall as the implantable medical device is delivered to the target location of the body vessel.

9. The delivery member of claim 1, further comprising:
a loop wire comprising a first end affixed to the body and comprising a loop opening positioned approximate a distal end of the compressed distal portion.

10. The delivery member of claim 9, wherein the loop wire is stretch resistant, and wherein the loop wire is under tension when the implantable medical device is secured to the delivery member.

11. The delivery member of claim 10, wherein the body further comprises a flexible coil disposed in a proximal direction from the compressed distal portion, wherein the loop wire inhibits elongation of the compressed distal portion.

12. The delivery member of claim 11, further comprising a sleeve that extends along a majority of the flexible coil.

13. A method comprising:
providing a body comprising a lumen extending therethrough, a compressible distal portion, and a support coil inner tube;
compressing the compressible distal portion;
extending a pull wire through the lumen;
securing a distal end of the pull wire to an implantable medical device; and
forming a pull wire portion of the pull wire to abut a sidewall of the support coil inner tube to provide a frictional resistance against the sidewall,
wherein the pull wire comprises a slack length at a proximal end of the pull wire and a straight portion distal of and approximate the slack length,
wherein a distal end of the pull wire comprises a straight portion, and
wherein the pull wire portion is proximal of and approximate the straight portion of the distal end of the pull wire.

14. The method of claim 13, further comprising:
inhibiting, through the frictional resistance of the pull wire portion against the sidewall, release of the implantable medical device while the implantable medical device is delivered through vasculature to a treatment site; and
providing a force sufficient to overcome the frictional resistance of the pull wire portion against the sidewall, thereby translating the pull wire proximally and releasing the implantable medical device at the treatment site.

15. The method of claim 13, further comprising:
affixing a loop wire to the body;
positioning a loop opening in the loop wire approximate a distal end of the compressible distal portion while the loop wire is affixed to the body such that the loop wire is extended through the lumen; and
extending the loop opening through a locking portion of an implantable medical device.

16. The method of claim 13, wherein the pull wire portion comprises a shaped feature selected from a trapezoidal-shaped feature, a triangular-shaped feature, a corkscrew-shaped feature, a knot-shaped feature, or a wave-shaped feature.

17. The method of claim 13, wherein the pull wire comprises a memory shape alloy.

18. The method of claim 14, wherein inhibiting release of the implantable medical device further comprises the pull wire portion remaining in contact with the sidewall as the implantable medical device is delivered to the treatment site.

19. The method of claim 13, further comprising:
coating the pull wire with a polytetrafluoroethylene coating; and
selectively removing the polytetrafluoroethylene coating from the pull wire portion.

20. The method of claim 13, wherein providing the body further comprises:
connecting a distal end of a proximal hypotube to a flexible coil;
connecting a distal end of the flexible coil to a proximal end of the compressible distal portion of the body;
connecting the proximal hypotube, flexible coil, and compressible distal portion to provide the body comprising a lumen extending through the proximal hypotube, flexible coil, and the compressible distal portion; and
positioning a sleeve to extend along a majority of the flexible coil, thereby inhibiting radial expansion of the flexible coil.

\* \* \* \* \*